United States Patent [19]

Lintott

[11] Patent Number: Plant 7,287

[45] Date of Patent: Jul. 31, 1990

[54] CHRYSANTHEMUM PLANT NAMED SIGLO

[75] Inventor: Keith G. Lintott, Sussex, England

[73] Assignee: Framptons Nurseries Ltd., West Sussex, England

[21] Appl. No.: 164,344

[22] Filed: Mar. 4, 1988

[51] Int. Cl.[5] ..... A01H 5/00

[52] U.S. Cl. ..... Plt./80

[58] Field of Search ..... Plt./80

*Primary Examiner*—Robert E. Bagwill

*Attorney, Agent, or Firm*—Brisebois & Kruger

[57] ABSTRACT

A new variety of *Chrysanthemum morifolium* Bailey of the pink spray type, known as "Siglo" and characterized by year-round flowering, vigorous growth, and good flower size.

1 Drawing Sheet

This invention relates to a new and distinct variety of *Chrysanthemum morifolium* Bailey (spray type) known as "Siglo".

My new variety "Siglo" is a new and distinct variety originated by me in Chichester, Sussex, England, from a cross made in 1984 between the variety Bijoux and a seedling number B191/9, the former being the seed parent and the latter being the pollen parent.

Siglo resulted from an extensive breeding program to produce improved varieties for year round Chrysanthemum production, particularly for winter production.

Siglo has the following improved characteristics over the variety Bijoux, the most similar year round spray type grown in Great Britain.

1. Siglo will flower year round i.e. weeks 1 to 52.
2. Siglo is more vigorous than Bijoux.
3. The flower size of Siglo is larger than Bijoux.
4. The response of Siglo is similar to Bijoux.

Asexual production of this new variety "Siglo" as performed in Sussex, England, by rooting vegetative shoots shows that the above characteristics are fixed and come true to type through succeeding generations.

The accompanying drawing shows a typical flower of my new variety depicted in color as nearly true as it is reasonably possible to make the same in a color illustration of this type.

The following is a detailed description of the new variety "Siglo" with color terminology in accordance with the Royal Horticultural Society Colour Chart, (R.H.S.).

Genus: Chrysanthemum.

Species: *Morifolium* Bailey.

Type: Spray.

Class: Quilled Anemone (Natural Chrysanthemum Society Section 11).

Breeding: A cross between the variety "Bijoux" and a seedling number B191/9, the former being the seed parent and the latter being the pollen parent.

Propagation: Holds its distinguishing characteristics through succeeding propagations by rooting vegetative shoots.

Flowers: As grown and observed in Sussex, England, 6 to 15 flowers are borne on pedicels, after removal of the main apical bud.

Bloom:

*Size.*—Diameter of 70 mm. to 90 mm. when fully open.

*Form.*—Quilled Anemone.

*Petalage.*—135 to 165 Ray petals. 45 to 65 Disc Petals.

*Form.*—Quilled Anemone.

*Petals.*—Medium/long, overlapping, spooned of medium texture.

*Pedicels.*—Medium and strong, 80 mm. to 150 mm. long.

*Color of open bloom.*—Inner face of fully expanded petal R.H.S. 69B. Outer face of fully expanded petal R.H.S. 69A. Inner face of young petal R.H.S. 65D. Outer face of young petal R.H.S. 65C.

*Response Group.*—8½ to 9 weeks.

*Temperature tolerance.*—13° C.-18° C. (56° F.-65° F.) at night.

Plant: Strong upright habit of growth, medium to tall.

Foliage: Good quality with average internode length of 2.5 cm; Medium size and medium texture; color R.H.S. 139A.

Stem: Upright, medium thickness and strong. Color R.H.S. 139A at flowering.

Water uptake: Good.

I claim:

1. A new and distinct variety of *Chrysanthemum morifolium* Bailey of the pink spray type substantially as herein shown and described, characterized particularly as to novelty by year-round flowering, vigorous growth, and good flower size.

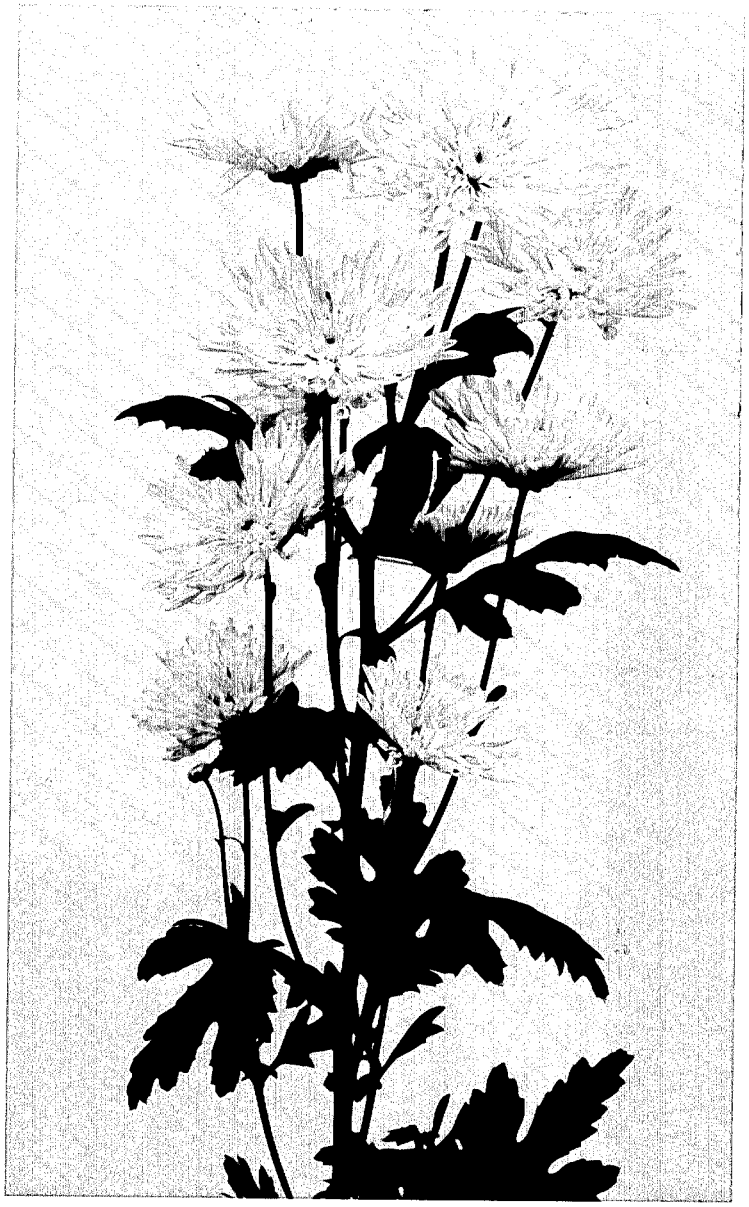

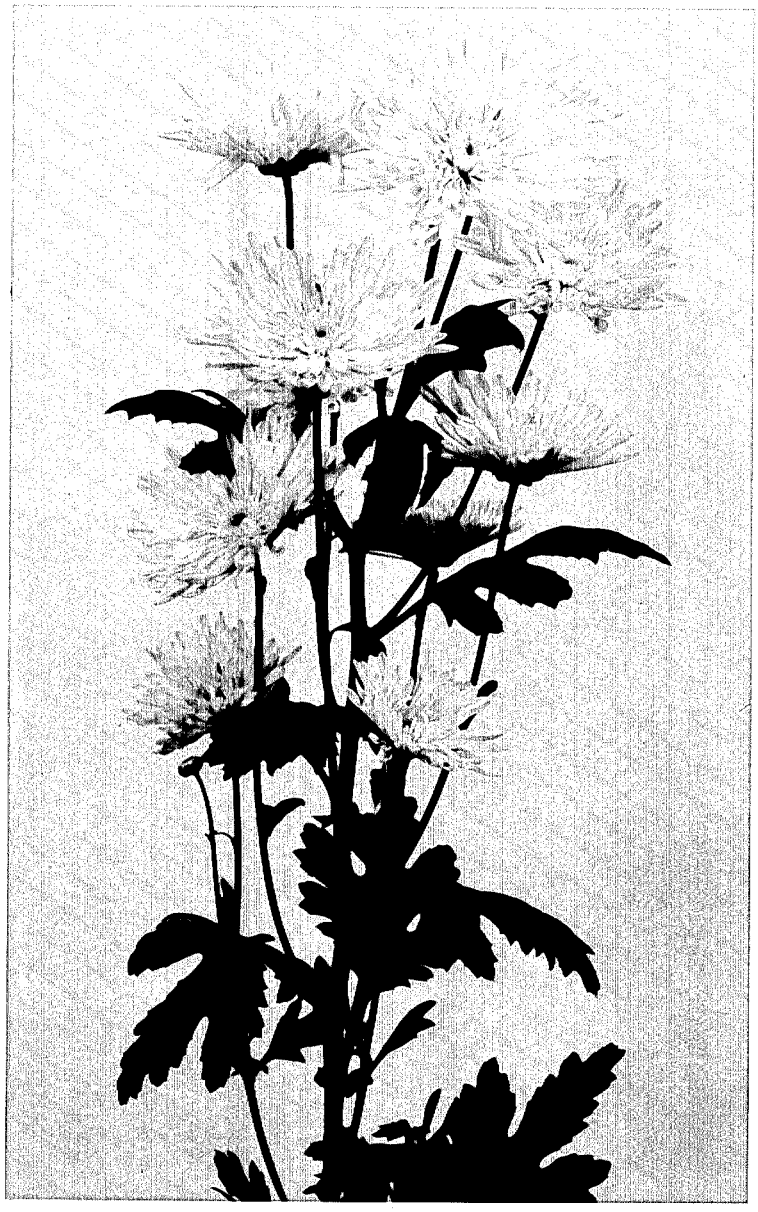

* * * * *